(12) United States Patent
Hornig et al.

(10) Patent No.: US 8,702,661 B2
(45) Date of Patent: Apr. 22, 2014

(54) DEVICE FOR FEEDING MEDICAL FLUIDS

(75) Inventors: Wolfgang Hornig, Kierspe-Bollwerk (DE); Bernhard Pech, Hünstetten (DE)

(73) Assignee: V. Krutten Medizinische Einmalgerate GmbH, Idstein (DE)

( * ) Notice: Subject to any disclaimer, the term of this patent is extended or adjusted under 35 U.S.C. 154(b) by 125 days.

(21) Appl. No.: 13/143,967

(22) PCT Filed: Jan. 15, 2010

(86) PCT No.: PCT/EP2010/000185
§ 371 (c)(1),
(2), (4) Date: Jul. 11, 2011

(87) PCT Pub. No.: WO2010/083962
PCT Pub. Date: Jul. 29, 2010

(65) Prior Publication Data
US 2011/0282303 A1 Nov. 17, 2011

(51) Int. Cl.
*A61M 5/00* (2006.01)
(52) U.S. Cl.
USPC ............ 604/248; 604/246; 604/537; 137/886
(58) Field of Classification Search
USPC .......... 604/284, 537, 539, 30, 32, 33, 167.01, 604/167.05, 246–249, 533–535, 538; 137/886; 251/215, 218
See application file for complete search history.

(56) References Cited

U.S. PATENT DOCUMENTS 4,421,507 A * 12/1983 Bokros ................... 604/539
5,370,624 A 12/1994 Edwards et al.

FOREIGN PATENT DOCUMENTS

| EP | 1555041 | 7/2005 |
| EP | 1627658 | 2/2006 |
| FR | 2772280 | 6/1999 |

* cited by examiner

*Primary Examiner* — Aarti B Berdichevsky
*Assistant Examiner* — Laura Schell
(74) *Attorney, Agent, or Firm* — Occhiuti & Rohlicek LLP

(57) ABSTRACT

The application relates to a device for feeding medical fluids, in particular for applying a pharmaceutical into the hose line of a transfer unit for enteral or parenteral nutrition. The device comprises a base body (1) having an inlet (1A) and an outlet (1B) and a rotatable closure body (2) which has an inlet (2A). The device is characterized in that the base body (1) comprises a hollow cylindrical attachment piece (4) ending in the passage (1E) of the base body between the inlet and outlet (1B, 1B), and the closure body comprises a cylindrical shut-off body (11) that is arranged in the closure body (2) such that the shut-off body (11) sits in the attachment piece (4) of the base body (1) in a sealing manner in a first position of the closure body (2), so that a fluid connection between the inlet (2A) of the closure body (2) and the passage (1E) of the base body (1) is interrupted, and does not sit in the attachment piece in a second position of the closure body, so that the fluid connection is established. In the device, the sealing is solely established in that the shut-off body of the closure body sits in the attachment piece of the base body. Thus, only one sealing surface is provided.

10 Claims, 3 Drawing Sheets

Figure 1:
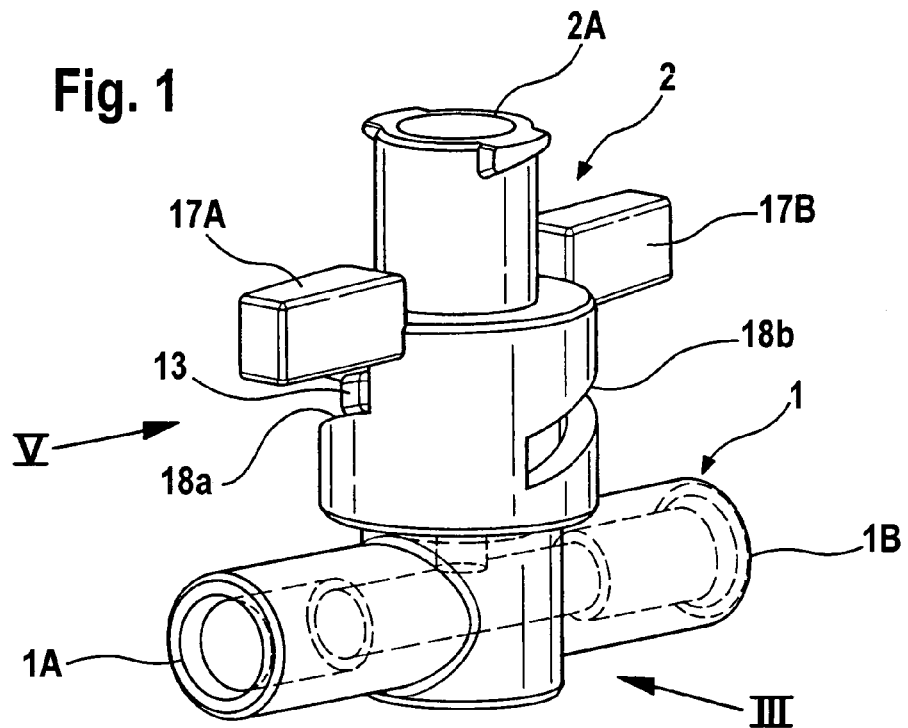

Fig. 3
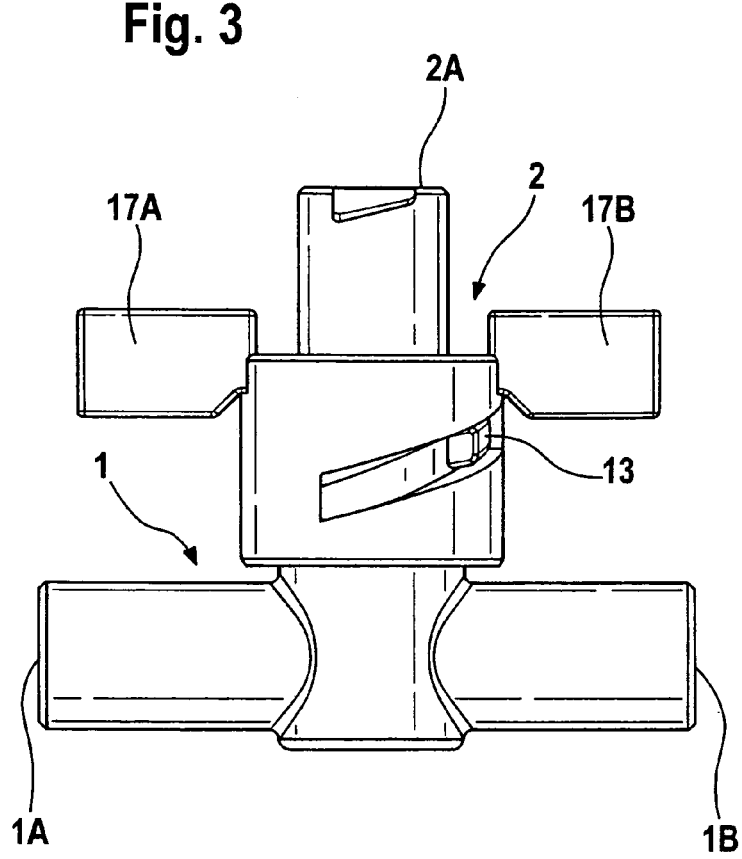
Fig. 5
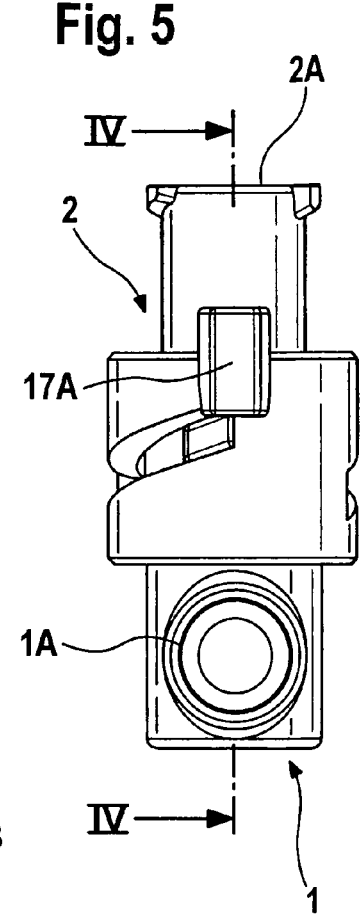
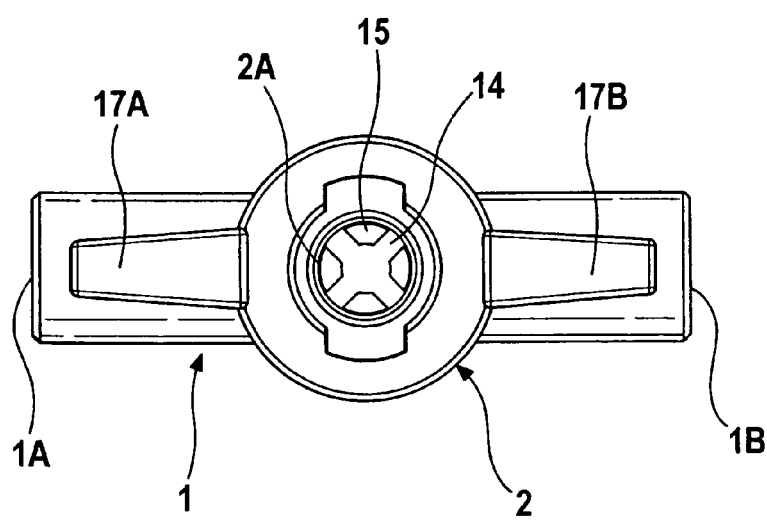
Fig. 4

DEVICE FOR FEEDING MEDICAL FLUIDS

CROSS-REFERENCE TO RELATED APPLICATIONS

This application is the National Stage of International Application No. PCT/EP2010/000185, filed on Jan. 15, 2010, which claims the priority of German Patent Application No. 10 2009 005 822.2, filed on Jan. 22, 2009. The contents of both applications are hereby incorporated by reference in their entirety.

The device relates to a device for feeding medical fluids, in particular for applying a pharmaceutical into the hose line of a transfer unit for enteral or parenteral nutrition.

Transfer units are used for enteral or parenteral nutrition, with which a nutrient solution is fed to a patient from a container. The known transfer units have a hose line with connectors, which are connected at one end to the nutrient solution container and at the other end to a feeding tube.

In some cases, with enteral or parenteral nutrition it is necessary to apply a medical fluid in the hose line of the transfer unit. Various devices are known for feeding pharmaceuticals into the hose line of the transfer unit.

The known devices consist of a base body and a closure body. The base body has an intake, to which one of the hose lines leaving the nutrient solution container is connected, and an outlet, to which the hose line leading to the patient is connected. The intake and outlet of the base body are connected to one another by a passageway, such that the nutrient solution can flow from the nutrient solution container to the patient. In order to apply a pharmaceutical, the closure body has an intake. The closure body can be rotated on the base body between a first position, in which a fluid connection between the intake of the closure body and the passageway of the base body is interrupted, and a second position, in which the fluid connection between the intake of the closure body and the passageway of the base body is established. During the enteral or parenteral nutrition, the closure body is in the first position. Only for the purpose of applying a pharmaceutical is the closure body rotated to the second position.

The device for feeding medical fluids should fulfill various requirements. Firstly, it must be ensured that the device is sealed securely, in order that no leakage can occur. Secondly, the closure body should be able to be rotated with a relatively small amount of force, in order that the device can be easily manipulated. Aside from the secure sealing and the ease of handling, relatively small construction expenditure is strived for, in order that the production costs be kept as low as possible.

A known device for feeding medical fluids of the applicant's is distinguished in that the base body has a hollow cylindrical appendage in which a hollow cylindrical section of the closure body is inserted in a tight fitting manner. In this manner, the outer surface of the hollow cylindrical section of the closure body is sealed against the inner surface of the hollow cylindrical appendage of the base body, such that a first sealing surface is obtained. To open and close the known three-way valves, the closure body is rotated in such a manner that the closure body moves upwards. For this, a cylindrical shut-off body, located on the base body, engages with the hollow cylindrical section of the closure body in such a manner that a second sealing surface is established. The known three-way valve has been shown to be effective in the field. It has been shown to have disadvantages however, in that there are two sealing surfaces, which must each be sealed securely. Furthermore, it is disadvantageous that the force required for rotating the closure body is relatively large, as the hollow cylindrical section of the closure body must sit relatively tightly in the hollow cylindrical appendage of the base body, in order that the closure body be securely sealed with respect to the base body. Further complicating things is the fact that both components lie tightly against one another over a relatively large surface.

The invention assumes the objective of creating a securely sealing and easily manipulated device, which allows for the feeding of medical fluids, in particular in a hose line of a transfer unit for enteral and parenteral nutrition to be applied.

The solution to this objective is attained according to the invention by means of the characteristics of claim 1. Advantageous embodiments of the invention are the subject matter of the dependent claims.

The device according to the invention for feeding fluids is distinguished in that the base body has a cylindrical shut-off component in the passageway opening into the hollow cylindrical appendage and the closure body, which is disposed in the closure body such that the shut-off component forms a seal in the appendage of the closure body when in the first position of the closure body, so that a fluid connection between the intake of the closure body and passageway of the base body is interrupted, and does not rest in the appendage when in the second position of the closure body, such that the fluid connection is established. With the device according to the invention therefore, a seal is established solely by means of the shut-off component of the closure body resting in the appendage of the base body. As a result, there is only one sealing surface. By this means, the risk of leakage is reduced. Because the only sealing surface between the shut-off component and the appendage can be designed to be relatively small, relatively small amounts of force are sufficient for rotating the closure body between the first and second positions. This simplifies the manipulation thereof.

When cylindrical or hollow cylindrical components are used in this context, it is understood that these are substantially cylindrical or hollow cylindrical components, as the components that seal against one another do not need to be designed as perfect cylinders. In this manner, the cylindrical components may be slightly conical in shape, in order to better form a seal. By way of example, the hollow cylindrical appendage of the base body and the cylindrical shut-off component may be slightly conical in order to obtain a particularly secure seal.

In a preferred embodiment of the device according to the invention, the closure body has an internal hollow cylindrical section, which encases the hollow cylindrical appendage of the base body. By this means, the closure body is attached to the base body, wherein the closure body can be rotated about the base body. It is advantageous that only the shut-off component of the closure body needs to be sealed in relation to the hollow cylindrical appendage of the base body, but not, however, the internal hollow cylindrical section of the closure body in relation to the hollow cylindrical appendage of the base body. Therefore, the closure body does not need to sit tightly on the base body, as a result of which the friction remains relatively minimal.

In a further particularly preferred embodiment, the shut-off component is attached in the internal hollow cylindrical section of the closure body with bridges, which, are connected at one end to the outer surface of the cylindrical shut-off component and at the other end to the inner surface of the internal hollow cylindrical section of the closure body. By this means, a sufficient cross-section remains in the closure body through which the medical fluids can flow. The shut-off component can also, however, be attached to the closure body with a disk shaped component, in which one or more holes are provided.

Another, particularly preferred embodiment provides that the base body has an external hollow cylindrical section, which encases the hollow cylindrical appendage of the base body, wherein the internal hollow cylindrical section of the closure body fits tightly in the gap between the external hollow cylindrical section and the hollow cylindrical appendage of the base body. By this means, the closure body is securely attached to the base body.

A further, particularly preferred embodiment provides that the closure body has an external hollow cylindrical section that overlaps the external hollow cylindrical section of the base body. The lifting motion caused by rotating the closure body is obtained preferably in that the external hollow cylindrical section of the closure body has at least one groove, in which at least one stud of the external hollow cylindrical section of the base body engages. In this manner, the groove may have different rises in its course along the circumference, which will affect the opening and closing characteristics. The groove extends preferably over a circumferential angle of 90°, such that the closure body can be rotated 90° about the base body. This rotational angle is fully sufficient for establishing an appropriate lifting motion. The rotational angle can however also be larger or smaller. It is only decisive that the closure body sits tightly in the appendage when in the first position. Preferably there are two grooves distributed about the circumference of the closure body, which each engage with a stud on the base body.

The device according to the invention is preferably designed as a T-component, wherein the intake of the closure body lies on an axis, which is perpendicular to the axis of the intake and outlet of the base body.

The closure body preferably has two radially protruding gripping elements, thus enabling the closure body to be easily held and rotated. Furthermore, the closure body preferably has a connection adapter designed as a Luer lock adapter, to which a corresponding Luer lock adapter can be connected. Instead of a Luer lock adapter, a Luer adapter can also be used if the adapter does not need to be secured by means of twisting. The intake and outlet of the base body are preferably designed as hollow cylindrical connection adapter in which a hose line can be inserted, which can be glued or welded to the base body. It is however also possible to use other connection adapters on the base body.

The device according to the invention is of particular use for the application of a pharmaceutical in the hose line of a transfer unit for enteral or parenteral nutrition. It is however also possible to use the device according to the invention for the application of a pharmaceutical in the hose line of an infusion system that is not used for enteral or parenteral nutrition.

In the following, embodiments of the invention shall be explained in greater detail with reference to the illustrations.

They show:

FIG. 1 An embodiment of the device according to the invention for the feeding of medical fluids in a perspective illustration, wherein the passageway in the base body is closed.

Figure 2:
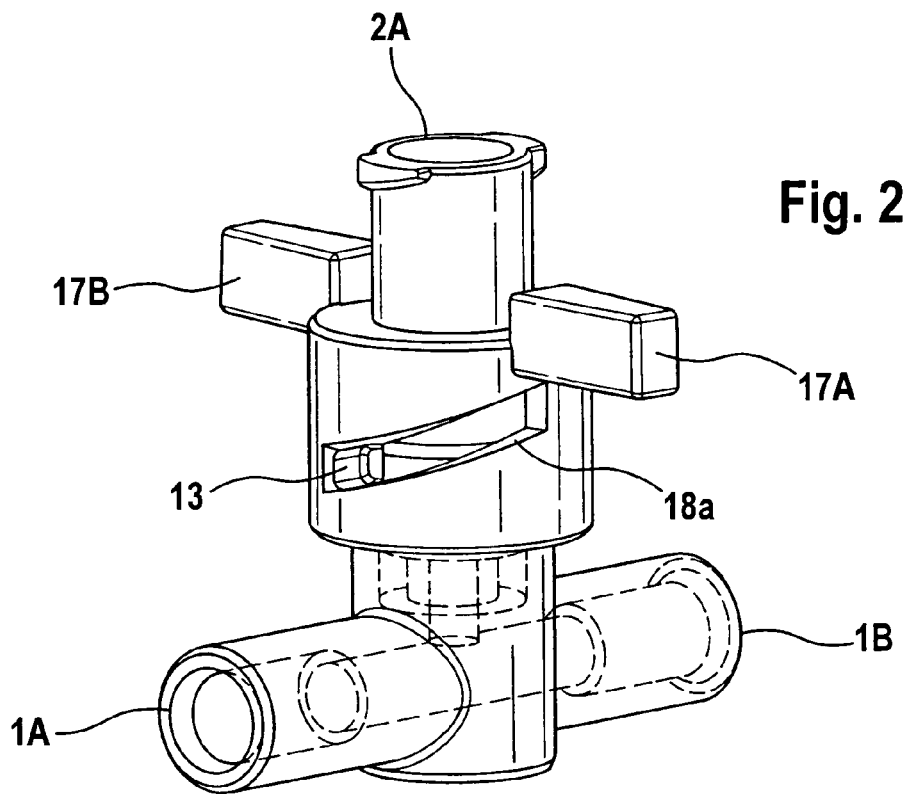

FIG. 2 The device in FIG. 1, wherein the passageway in the base body is open.

FIG. 3 The device in FIG. 1, shown from the perspective of arrow III.

FIG. 4 A top view of the device in FIG. 1.

FIG. 5 The device in FIG. 1, shown from the perspective of arrow V

Figure 6:
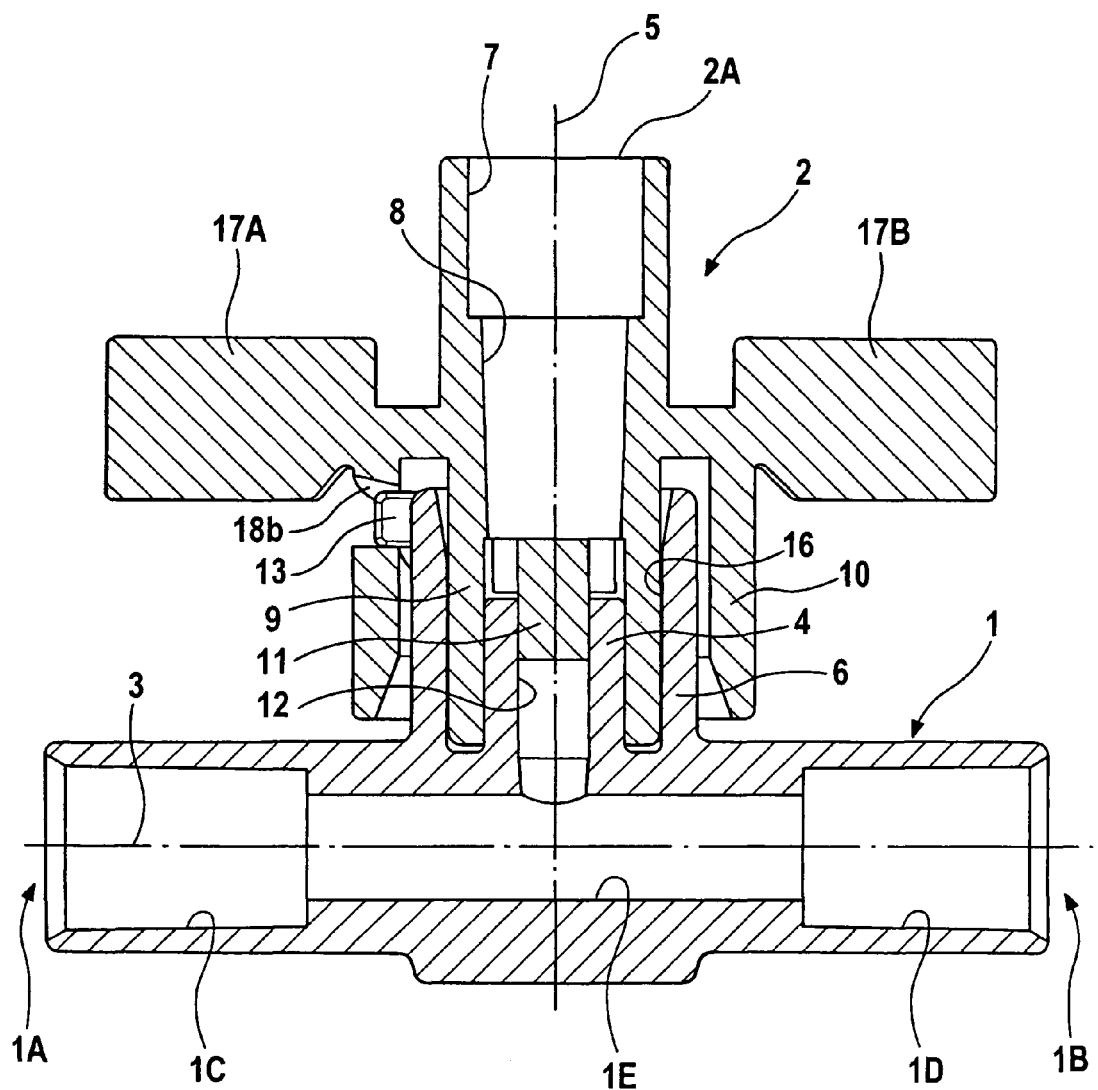

FIG. 6 A cross-section of the device in FIG. 1, cut along the line VI-VI in FIG. 5, enlarged.

FIGS. 1 and 2 show perspective illustrations of an embodiment of the device according to the invention for the application of a pharmaceutical in the hose line (not shown) of a transfer unit (not shown) for enteral or parenteral nutrition. The application device has a base body 1 and a closure body 2. The base and closure bodies 1, 2 are injection molded components, which can be mass-produced cost efficiently.

FIGS. 3-5 show the application device in side and top views, while FIG. 6 shows a cut-away view through the device in an enlarged image.

The base body 1 has an intake 1A and an outlet 1B, which lie on a common axis 3. The intake and the outlet are designed as hollow cylindrical connection adapters 1A, 1B, in which the end of a hose line can be inserted. For this, the respective hose line end can be glued or welded into the connection adapter 1A, 1B. Preferably, the holes 1C, 1D in the connection adapters are conical. There is a cylindrical passageway 1E with a smaller cross-section than the conical holes 1C, 1D of the two connection adapters 1A, 1B between the intake 1A and the outlet 1B.

Centrally located between the connection adapters 1A, 1B in the base body 1, there is a hollow cylindrical appendage 4, which opens into the passageway 1E of the base body. The longitudinal axis 5 of the appendage 4 is perpendicular to the axis 3, which passes through the connection adapters 1A, 1B. The hollow cylindrical appendage 4 of the base body 1 is encased by an external hollow cylindrical section 6, which extends upwards over the hollow cylindrical appendage 4, by means of the formation of a gap 16.

The closure body 2 has an intake 2A, designed as a hollow cylindrical connection adapter on which a device (not shown) can be connected for the application of a pharmaceutical. The connection adapter 2A may be a female Luer lock adapter. Luer lock adapters of this type belong to the prior art. The connection adapter 2A has a cylindrical section 7 for the purpose of connecting, for example, an oral syringe or a step adapter, wherein a conical section 8 for Luer syringes connects to the cylindrical section 7.

Beneath the conical section 8 of the connection adapter 2A, a hollow cylindrical section 9 is connected, which sits in a rotational manner in the gap 16 between the hollow cylindrical appendage 4 and the external hollow cylindrical section 6 of the base body 1.

The closure body 2 furthermore has an external hollow cylindrical section 10, which overlaps the external hollow cylindrical section 6 of the base body 1. The external hollow cylindrical section 10 of the closure body has two grooves 18a, 18b, disposed circumferentially, which extend over a circumferential angle of 90°. Studs, which are located on the external hollow cylindrical section 6 of the base body, rest in each of the grooves 18a, 18b. Only one of the two studs 13 can be distinguished in the figures, as the other stud lies on the opposite side. The grooves and studs form a sliding guide, designed such that the closure body can be rotated 90° on the base body between the two positions shown in FIGS. 1 and 2, respectively. In doing this, the base body rises and falls. In these two positions, the studs of the base body move between the two ends of the respective grooves.

A cylindrical shut-off component 11 is located in the center of the lower hollow cylindrical section 9 of the closure body 2, with which the lumen 12 of the appendage 4 can be closed. The cylindrical shut-off component 11 is a plug located in the center of the closure body 2. The shut-off component 11 is attached to the closure body 2 by means of four bridges 14 located circumferentially about said, which are connected to the outer surface of the shut-off component 11 on one end, and the inner surface of the hollow cylindrical section 9 of the closure body 2 at the other end, such that the fluids can flow through the passageways 15 formed between the bridges 14 (FIG. 4).

FIG. 6 shows the closure body 2 in the position in which the appendage 4 of the base body 1 is closed by the shut-off component 11 of the closure body 2 (FIG. 1). The shut-off component 11 rests in a sealing manner within the lumen 12 of the appendage 4. When the closure body 2 is rotated counter-clockwise 90° from the first position to the second position (FIG. 2), the closure body moves in an upwards direction. The sliding guide is designed such that the shut-off component 11 of the closure body 2 is fully extracted from the lumen 12 of the appendage 4 when in the second position. As a result, a flow connection is established between the intake 2A of the closure body 2 and the passageway 1E of the base body 1. The fluids can flow through the cylindrical section 7, the conical section 8, the passageway 15 and the lumen 12 in the passageway 1E. When the closure body 2 is then rotated clockwise 90° (FIG. 1), the shut-off component 11 is again pushed into the lumen 12 of the appendage 4, such that the fluid connection is again interrupted.

In order to better be able to hold the closure body, two radially protruding gripping elements 17A and 17B are provided. When the flow connection between the intake 2A of the closure body 2 and the passageway 1E of the base body 1 is interrupted, the two gripping elements 17A, 17B extend along the longitudinal axis of the base body (FIG. 1), while the gripping elements 17A, 17B are disposed at a right angle to the longitudinal axis of the base body when the flow connection between the intake 2A of the closure body 2 and the passageway 1E of the base body 1 is established. The flow connection between the intake 1A and the outlet 1B of the base body 1 remains active independently of the position of the closure body 2.

The invention claimed is:

1. A device for feeding medical fluids, in particular for the application of a pharmaceutical in the hose line of a transfer unit for enteral or parenteral nutrition, having a base body with a passageway, which connects an intake and an outlet of the base body, and a closure body disposed on the base body, having an intake, wherein the closure body is rotatable on the base body between a first position, in which the fluid connection between the intake of the closure body and the passageway of the base body is interrupted, and a second position, in which the fluid connection is established between the intake of the closure body and the passageway of the base body, characterized in that the base body has a hollow cylindrical appendage opening into the passageway, and the closure body has a cylindrical shut-off component located in the closure body such that the shut-off component rests in a sealing manner in the appendage of the base body when in the first position, such that the fluid connection between the intake of the closure body and the passageway of the base body is interrupted, and the shut-off component does not rest in the appendage of the base body when in the second position, such that the fluid connection is established between the intake of the closure body and the passageway of the base body.

2. The device according to claim 1, wherein the closure body has an internal hollow cylindrical section which encases the hollow cylindrical appendage of the base body.

3. The device according to claim 2, wherein the shut-off component is attached in the internal hollow cylindrical section of the closure body with bridges, which are connected to an outer surface of the shut-off component on one end, and to an inner surface of the internal hollow cylindrical section of the closure body at the other end.

4. The device according to claim 2, wherein the base body has an external hollow cylindrical section, which encases the hollow cylindrical appendage, wherein the internal hollow cylindrical section of the closure body fits tightly in a gap between the external hollow cylindrical section of the base body and the hollow cylindrical appendage of the base body.

5. The device according to claim 4, wherein the closure body has an external hollow cylindrical section overlapping the external hollow cylindrical section of the base body.

6. The device according to claim 5, wherein the external hollow cylindrical section of the closure body has at least one groove with which at lease one stud on the external hollow cylindrical section of the base body engages, wherein a path of the groove is structured such that the closure body exhibits an up or down motion when said is rotated.

7. The device according to claim 1, wherein the intake and outlet of the base body lie on a common axis, wherein the intake of the closure body lies on an axis perpendicular to the axis running through the intake and outlet of the base body.

8. The device according to claim 1, wherein the closure body has two gripping elements, which protrude radially from the closure body.

9. The device according to claim 1, wherein the intake of the closure body is designed as a Luer lock adapter.

10. The device according to claim 1, wherein the intake and outlet of the base body are designed as hollow cylindrical connection adapters for the insertion of a hose line.

* * * * *